United States Patent [19]

Weyl et al.

[11] 4,057,477
[45] *Nov. 8, 1977

[54] DEVICE FOR ELECTROCHEMICALLY MEASURING THE CONCENTRATION OF OXYGEN IN COMBUSTION GASES

[75] Inventors: Helmut Weyl, Schwieberdingen; Leo Steinke, Hegnach, both of Germany

[73] Assignee: Robert Bosch GmbH, Stuttgart, Germany

[*] Notice: The portion of the term of this patent subsequent to June 1, 1993, has been disclaimed.

[21] Appl. No.: 654,918

[22] Filed: Feb. 3, 1976

Related U.S. Application Data

[63] Continuation of Ser. No. 447,330, March 1, 1974, Pat. No. 3,960,693.

[30] Foreign Application Priority Data

Mar. 28, 1973 Germany .............................. 2315444

[51] Int. Cl.[2] ............................................ G01N 27/46
[52] U.S. Cl. ................................................ 204/195 S
[58] Field of Search ............................ 204/1 S, 195 S

[56] References Cited

U.S. PATENT DOCUMENTS

| | | | |
|---|---|---|---|
| 3,835,012 | 9/1974 | Hemak | 204/195 S |
| 3,841,987 | 10/1974 | Friese et al. | 204/195 S |
| 3,844,920 | 10/1974 | Burgett et al. | 204/195 S |
| 3,847,778 | 11/1974 | Riddel | 204/195 S |
| 3,891,529 | 6/1975 | Beesch | 204/195 S |

Primary Examiner—T. Tung
Attorney, Agent, or Firm—Michael J. Striker

[57] ABSTRACT

A housing of the device has a passage formed with two spaced open ends and with an inner circumferential shoulder. A tubular member of ion-conducting solid electrolyte material has a first closed-ended portion projecting from one of the open ends, and a second portion extending through the passage and being formed with an outer circumferential flange an axial end face of which faces the one open end and is supported by the shoulder. The interior of the tubular member is in communication with the ambient atmosphere, and an electron-conductive inner electrode is provided on an inner surface of the tubular member and conductively connected with an outside terminal portion. An electron-conductive outer electrode is provided on an outer surface of the tubular member and conductively connected with the housing. A compensating arrangement is provided on the housing fixed with reference thereto and engages the second portion of the tubular member in such a way as to compensate for differential coefficience of thermal expansion and contraction of the material of the housing and of the tubular member, respectively. This prevents relative movements of the housing and tubular member when such differential expansion or contraction occurs.

5 Claims, 4 Drawing Figures

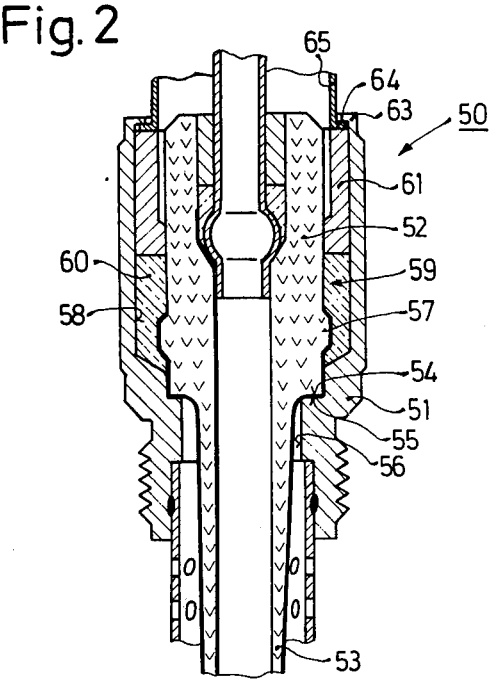
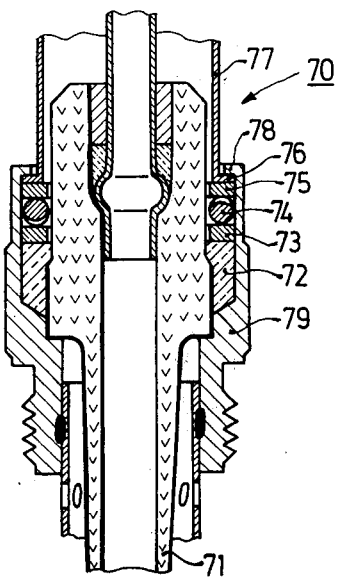
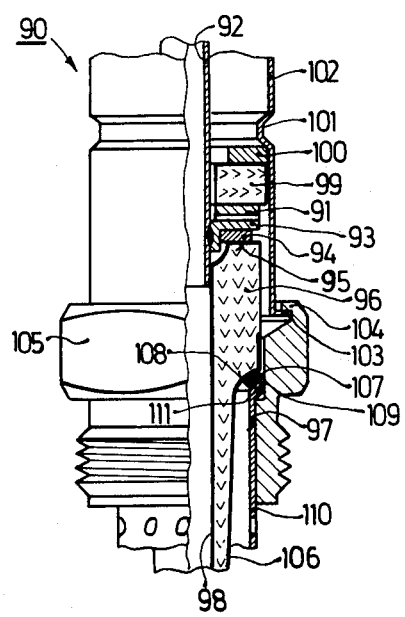

4,057,477

DEVICE FOR ELECTROCHEMICALLY MEASURING THE CONCENTRATION OF OXYGEN IN COMBUSTION GASES

CROSS-REFERENCE TO RELATED APPLICATION

This is a continuation of application Ser. No. 447,330, filed Mar. 1, 1974, now U.S. Pat. No. 3,960,693.

BACKGROUND OF THE INVENTION

The present invention relates to a device for electrochemically measuring the concentration of oxygen in combustion gases, particularly in combustion gases originating in internal combustion engines.

It is known to measure the content of oxygen in combustion gases, particularly but not exclusively those originating in internal combustion engines, by providing an electrochemical measuring device which has an oxygen reference electrode and is in part exposed to the stream of combustion gas and in part to the ambient atmosphere, with the result that the different concentrations of oxygen in the ambient atmosphere and in the stream of gas, respectively, cause a differential current flow which is indicative of the oxygen concentration in the combustion gas. Devices of this type, which operate on the principle of the oxygen concentration chain and use an ion-conductive solid electrolyte, are already known in the art, U.S. Pat. No. 3,514,377, G. B. Pat. No. 1,266,296. They are installed so that they extend in part into the stream of combustion gas. If such as device is used in an automative vehicle having a combustion engine, then the device is installed in the outlet manifold or discharge pipe through which the combustion gases flow. It is then subjected to the high temperature of the combustion gases which may reach temperatures in excess of 1000° C. The known devices are not generally capable of withstanding such temperatures.

A further drawback of the known devices of the type in question is that they use a solid-electrolyte tube which is mounted in the housing of the device, and experience has shown that in the prior-art devices it is difficult to so mount the electrolyte due in the housing that no relative movement and loosening will occur. This is due to the fact that the material of the housing on the one hand and that of the solid electrolyte tube on the other hand have different coefficients of thermal expansion and contraction, which over a period of time lead to loosening of the solid electrolyte tube in the housing, thereby causing gas leakage and improper electrical contact. Attempts have been made in the prior art to use a more or less elastic packing which is electrically conductive and is to be interposed between the housing and the solid electrolyte tube. However, primarily because of the vibrations to which such devices are subjected when installed in an automative vehicle, it has been found that this also does not provide a permanently satisfactory mounting of the solid electrolyte tube in the housing, that is a mounting which could assure over the lifetime of the device that no loosening can occur.

SUMMARY OF THE INVENTION

Accordingly, it is an object of the present invention to provide a device for electrochemically measuring the concentration of oxygen in combustion gases, which is not possessed of the aforementioned disadvantages.

An additional object of the invention is to provide such as device which is relatively simple in its construction and highly reliable.

In keeping with these objects, and with others which will become apparent hereafter, one feature of the invention resides in a device for electrochemically measuring the concentration of oxygen in combustion gases, particularly those of internal combustion engines. Briefly stated, the device comprises a housing having a passage which is formed with two spaced open ends and with an inner circumferential shoulder intermediate these ends. A tubular member of ion-conducting solid electrolyte material has a closed-ended first portion which projects from one of the open ends, and a second portion which extends through the passage and is formed with an outer circumferential flange an axial end face of which faces the one open end and is supported by the shoulder. The interior of the tubular member is in communication with the ambient atmosphere and the first portion will in use be exposed to a flow of combustion gases. The materials of the housing and of the tubular member have differential coefficients of thermal expansion and contraction. An electron-conductive inner electrode is provided on an inner surface of the tubular member and is conductively connected with an outside terminal portion. An electron-conductive outer electrode is provided on an outer surface of the tubular member and conductively connected with the housing. Compensating means is mounted on the housing fixed with reference thereto and engages the second portion of the tubular member. The compensating member is operative to compensate for the differential coeffocients of the material of the housing and of the tubular member, respectively, in order to prevent relative movements of the housing and tubular member.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 2 is a fragmentary section similar to FIG. 1, illustrating a second embodiment of the invention;

FIG. 3 is a view similar to FIG. 2, but illustrating a third embodiment of the invention; and FIG. 4 is a view analogous to FIG. 3 but illustrating yet a further embodiment of the invention.

DESCRIPTION OF THE PREFERRED EMBODIMENTS

Figure 1:
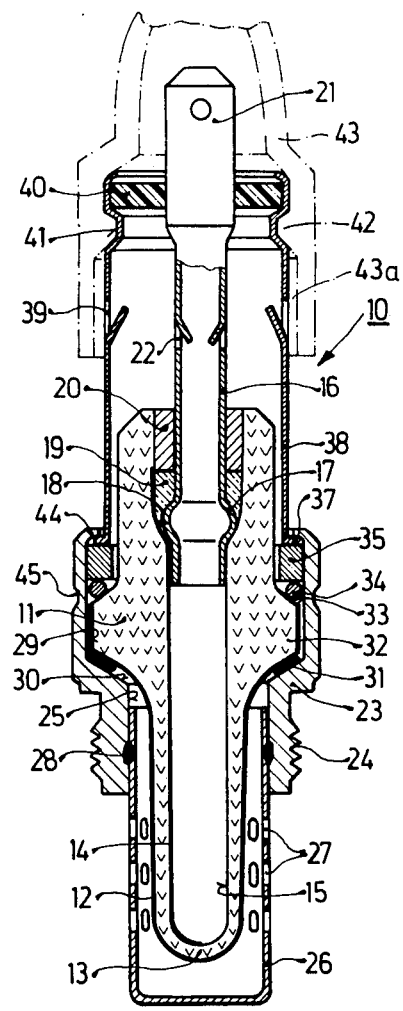
FIG. 1 is an enlarged-scale axial section through one embodiment of the invention.

Referring firstly to FIG. 1 of the drawing, it will be seen that the device for electrochemically measuring the concentration of oxygen in combustion gases which is shown in this FIGURE, is identified with reference numeral 10 in toto. It is provided with a tubular member 11 one end of which is closed and which is of an ion-conducting solid electrolyte material, for instance zirconium dioxide, thorium dioxide, mullite. On its outer surface the tubular member 11 is provided with an electron-conducting catalyst layer 12, such as platinum, platinum metals, copper-chromium-oxide, lanthanun-cobalt-oxide, and on its inner surface it is provided with a similar layer 14, for instance again of platinum or noble metals, which extends to the bottom wall 13 of the tubular member 11. It will be understood that when the device is installed for operation, for instance in the outlet manifold of a combustion engine, the portion of the tubular member which has the closed end — and hence the layer or electrode 12 — will be exposed to the stream of combustion gases, whereas the interior 15 of the tubular member 11, and hence the electrode or layer 14, will be exposed to the ambient atmosphere in the manner still to be described. This exposure to the gas stream and the ambient atmosphere, respectively, is conventional and known from the art.

A tubular terminal member 16 is provided which extends into the interior 15 of the tubular solid-electrolyte member 11, from the open end of the latter. The terminal member 16 is formed with an annular head 17 which engages and is supported by a rounded shoulder 18 formed in the interior 15 where the latter is provided with an enlargement. This enlargement accommodates an electrically conductive glass melt 19 of known type (U.S. Pat. No. 3,360,676), and is finally closed at the outer end with a metallic annular member 20. The melt 19 and the member 20 retain the member 16 rigidly and fixedly connected with the member 11, and also serves to provide for an electrical contacting between the layer 14 and the member 16. The latter has a free end which is configured as a plugin terminal 21, and forwardly of this free end the member 16 is formed with one or more (two illustrated) air inlet openings 22 which in operation will communicate with the ambient atmosphere so that the latter in turn can communicate with the interior of the tubular member 11.

The members 11 and 16 are connected with a metallic housing 23 which is advantageously composed of a heat and scale-resistant metallic material for instance ferritic steel. The housing 23 surrounds the middle portion of the member 11 and is provided on its exterior in the region of that end where the closed end of the member 11 is located, with screw threads 24 by means of which it can be threaded into a tapped bore provided for this purpose in a conduit, such as the exhaust manifold of a combustion engine. The housing 23 has a center passage 25 which is open at both ends an in which there is accommodated a protective sleeve 26 which also is of a material resistant to heat and scale, for instance chromium-nickel-steel, and which surrounds the closed end portion of the solid-electrolyte tubular member 11. The sleeve 26 is provided with a plurality of openings 27 through which the combustion gas can enter and contact the layer 12. The sleeve 26 is connected with the housing 23 in suitable manner, for instance by several spot welds 28 as illustrated in FIG. 1.

The passage 25 of the housing 23 is enlarged at 29 so that at the juncture between the larger-diameter and smaller-diameter portions of the passage there is formed an annular shoulder 30. Placed on this shoulder is a ring 31 composed of relatively soft material, for instance pure nickel, and a flange 32 formed at the exterior of the tubular member 11 is in contact with this ring which provides a seal between the housing 23 and the tubular member 11 and which additionally provides for electrical contact between the housing 23 and the layer 12. The reason for using relatively soft material is to assure that no damage occurs to the tubular member 11, for instance due to breakage. The opposite axial end face 33 of the flange 32 also has a ring 34 superimposed upon it. This ring is similarly of relatively soft material such as pure nickel, for the reasons just outlined above, an is in contact with an annular member 35 which has a thermal expansion coefficient intermediate those of the member 11 and the housing 23 and thus constitutes a compensating element serving to compensate for the differential thermal expansion and contraction of the material of the tubular member 11 on the one hand and of the housing 23 on the other hand. Axially adjacent the annular member 35 is the annular flange 37 of a metallic tube 38 which is a protective tube and so concentrically surrounds the portion of the tubular member 11 which projects upwardly in FIG. 1, and also the terminal element 16, that only the contact or contact-shaped terminal portion 21 extends out of the protective tube 38. The latter is provided in its circumference with a plurality of air inlet openings 39 through which ambient air can enter. Its upper free end in FIG. 1 accommodates the disc of insulating material 40 which tightly surrounds the contact portion or terminal portion 21 and closes this end of the protective tube 38. The disc is retained by forming a groove 41 in the circumference of the protective tube 38. A connecting sleeve 43 is shown diagrammatically in broken lines and formed with an inner annular bead 42 which can snap into this groove 41.

It should be noted that that portion of the sleeve 43 located between the bead 42 and the free end of the sleeve 43 surrounds the tube 38 at a distance 43a, but overlaps the apertures 39. This makes it possible for air to enter through these apertures 39 but prevents very largely any possibility that rain water or the like might splash into these apertures. The components 31, 32, 34, 35 and 37 which axially follow one another in the enlarged portion 29, are retained in axial direction by an inwardly bent rim or bead 44 on the housing 23, and are drawn tightly together in the region 45 by shrink fitting or the like. The compensating member 35 is of a material which compensates for the differential coefficient of thermal expansion and contraction of the members 11 and 23, respectively. In other words, at various temperatures the degree of expansion or contraction of the material of the member 35 will counteract the contraction or expansion of the housing 23, the flange 32, the rings 31 and 34 and the flange 37, which all cooperate with the member 35. This reliably prevents any loosening of the member 11 in the housing 23. It is currently preferred that the member 35 be austenitic steel and that the housing 23 be ferritic steel.

The embodiment of FIG. 2 corresponds largely to that of FIG. 1. However, the device 50 which is shown in FIG. 2 differs from the device 10 of FIG. 1 in that the seal between the housing 51 and the solid-electrolyte tubular member 52, and the contacting between the housing 51 and the catalyst layer 53 at the outer side of the tubular member 52, are different.

In FIG. 2 the solid-electrolyte tubular member 52 has a shoulder 54 which engages a corresponding shoulder 55 formed in the center passage 56 of the housing. A flange 57 is formed on the tubular member 52 and extends into a space 59 which is formed between the tubular member 52 and the enlarged portion 58 of the passage 56. This space, identified with reference numeral 59, is filled with a pulverulent sealing mass or body 60, which preferably is electrically conductive (e.g., graphite, copper powder). Also accommodated in this space 59 is an annular compensating member 61. An inwardly directed rim 63 at the upper open end (FIG. 2) of the housing 51 presses against the member 61 and thereby upon the material 60. In addition, it also retains the flange 64 of a protective tube 65.

In accordance with the invention the annular member 61, also, is composed of a material the coefficient of thermal expansion and contraction will counteract the differential thermal expansion and contraction of the components 51, 60 and 52, at least to a large extent. In the embodiment of FIG. 2 the material 60 retains the tubular member 52 against radial movement. The annular member 61 is so constructed that its thermal expansion so compensates the thermal expansion of the housing 51, the tubular member 52 and the material 60 that the material 60 will fill the space surrounded by the housing 51, the tubular member 52 and the annular member 61 at a pressure which acts upon the material 60 and is largely constant. Electrical contact between the layer 53 on the tubular member 52 and the housing 51 is the result of direct engagement between the shoulder 54 and the shoulder 55, and also via the electrically conductive material 60.

FIG. 3 shows a further embodiment wherein the device in toto is identified with reference numeral 70. Here, the device has a solid-electrolyte tubular member 71 which is retained against radial movement by a pulverulent mass 72. An annular member 73 overlies the mass 72, and overlying the member 73 and surrounding the tubular member 72 as does the member 73, is a spring element (spring washer of any configuration) which serves the compensating function of the elements 35 and 61 of the preceding embodiment.

The spring element 74 is of a heat resistant material for instance chromium-nickel-steel and bears via an additional annular member 75 and the flange 76 of a protective tube 77 upon the inwardly extending rim 78 of the housing 79. Its purpose is of course the same as in the other embodiments, namely to compensate for the differential thermal expansion behavior of the tubular member 71, the housing 79 and the material of the mass 72.

Since in all other respects the embodiment in FIG. 3 corresponds to that of FIG. 2, a further description will not be required.

Coming, finally, to the embodiment in FIG. 4 it will be seen that here the device per se is identified with reference numeral 90. Analogously to the embodiment of FIG. 3, that of FIG. 4 also uses an annular spring element 91 for instance a cup spring to perform the compensating function according to the present invention. In this embodiment, the spring element 91 bears via a flange 93 that is welded to the member 92 which corresponds to the member 16 of FIG. 1, and a ring 94 of relatively soft material, such as pure nickel, upon the rear end face 95 of the solid-electrolyte tubular member 96. An electron conductive layer 98 of the tubular member 96 which is located in the housing passage 97 extends in this embodiment not only longitudinally of the tubular member 96, but also overlies the rear end 95 and is thus in conductive contact with the member 92.

In addition to the spring element 91, the member 92 is also surrounded by a ceramic-material insulating ring 99 and by a metal ring 100 which is fixed with respect to the protective tube 102 by forming a depression in the outer surface of the tube 102, to obtain the internal abutment identified by reference numeral 101. A flange 103 of the tube 102 is engaged and retained by the inwardly extending rim 104 of the housing 105.

A ring 107 which is again of relatively soft material, for instance pure nickel, engages the shoulder 108 of the tubular member 96 and is indirectly supported —via a protective sleeve 110 — by a shoulder 109 formed in the central passage 97 of the housing. The purpose of the ring is to provide a seal between the housing 105 and the tube 96, as well as to provide for electrical contact between the housing 105 and the catalyst layer 106 on the outer side of the tubular member 96.

As compared to the embodiments of FIGS. 1-3, that shown in FIG. 4 shows a further difference, namely an advantageous manner of retaining the protective sleeve 110 which surrounds the free end of the tubular member 96 that is to be exposed to the flow of combustion gases. The protective sleeve 110 is formed at its inner or rear open end with a flange 111 which is clampingly pressed against the hosing 105 by the shoulder 108 of the solid-electrolyte tubular member 96.

It should be understood that the manner in which the protective sleeve 110 is mounted in FIG. 4, could be analogously employed in the embodiments of FIGS. 1-3 also. Furthermore, it should also be understood that as an alternative to contacting the rear end face 95 of the tubular member 92, it is also possible to use a spring element such as the element 91 to exert pressure upon a flange of the tubular member 96 in FIG. 4, analogous to the construction as shown in FIG. 1. It will also be appreciated that it is conceivable to make the housing 105 longer than shown in FIG. 5, and to have its inwardly extending rim 104 engage the ring 100, instead of the inwardly extending bead formed by the depression 101. In that case, the tubular protective member 102 would have to be secured in a different way. In all embodiments, the solid-electrolyte material of the respective tubular member can be zirconium dioxide, thorium dioxide or mullite, and the outer electron-conductive layer can be platinum, one of the other platinum metals, copper-chromium-oxide or lanthanum-cobalt-oxide, and the inner electron-conductive layer can be platinum or a other noble metal. Where as sealing material is used, such as the pulverulent material described before, it may advantageously be of graphite.

It will be understood that each of the elements described above, or two or more together, may also find a useful application in other types of constructions differing from the types described above.

While the invention has been illustrated and described as embodied in a device for electrochemically measuring the concentration of oxygen in combustion gases, it is not intended to be limited to the details shown, since various modifications and structural changes may be made without departing in any way from the spirit of the present invention.

Without further analysis, the foregoing will so fully reveal the gist of the present invention that other can by applying current knowledge readily adapt it for various applications without omitting features that, from the standpoint of prior art fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. A device for electro-chemically measuring the concentration of oxygen in combustion gases, particularly those of internal combustion engines, comprising a housing having a passage which is formed with two spaced open ends with an inner circumferential shoulder intermediate said ends and with a radially inwardly extending rim in the region of one of said open ends; a tubular member of ion-conducting solid electrolyte material having a closed-ended first portion which projects from the other of said open ends, and a second portion which extends through said passage and is formed with an outer circumferential flange of which one axial end face faces towards said other open end and is supported by said shoulder and of which another axial end face faces away from said other open end, the interior of said tubular member being in communication with the ambient atmosphere and the exterior of said first portion being adapted for exposure to a flow of combustion gases, and the materials of said housing and of said tubular member having differential coefficients of thermal expansion and contraction; an electron-conductive inner electrode on an inner surface of said tubular member and being conductively connected with an outside terminal portion; an electron-conductive outer electrode on an outer surface of said tubular member and being conductively connected with said housing; compensating means comprising a discrete annular compensating member installed in said housing separate from but fixed with reference thereto and being confined between said rim and said flange of said tubular member in surrounding engagement with said second portion of said tubular member, said compensating means being of a material having a coefficient of thermal expansion and contraction which compensates for said differential coefficients of said housing and of said tubular member so as to prevent development of cracks or loosening of the seal between said housing and said tubular member; and a body of pulverulent material accommodated in and filling a space defined by said tubular member, housing and annular member, said body being at substantially constant pressure despite the occurrence of differential thermal expansion or contraction due to said differential coefficients.

2. A device for electro-chemically measuring the concentration of oxygen in combustion gases, particularly those of internal combustion engines, comprising a housing having a passage which is formed with two spaced open ends with an inner circumferential shoulder intermediate said ends and with a radially inwardly extending rim in the region of one of said open ends; a tubular member of ion-conducting solid electrolyte material having a closed-ended first portion which projects from the other of said open ends, and a second portion which extends through said passage and is formed with an outer circumferential flange of which one axial end face faces towards said other open end and is supported by said shoulder and of which another axial end face faces away from said other open end, the interior of said tubular member being in communication with the ambient atmosphere and the exterior of said first portion being adapted for exposure to a flow of combustion gases, and the materials of said housing and of said tubular member having differential coefficients of thermal expansion and contraction; an electron-conductive inner electrode on an inner surface of said tubular member and being conductively connected with an outside terminal portion; an electron-conductive outer electrode on an outer surface of said tubular member and being conductively connected with said housing; compensating means comprising a discrete annular compensating member installed in said housing separate from but fixed with reference thereto and being confined between said rim and said flange of said tubular member in surrounding engagement with said second portion of said tubular member, said compensating means being of a material having a coefficient of thermal expansion and contraction which compensates for said differential coefficients of said housing and of said tubular member so as to prevent development of cracks or loosening of the seal between said housing and said tubular member; a first ring of relatively soft material accommodated intermediate one of said axial end faces and said shoulder; and a second ring of relatively soft material accommodated intermediate the other of said axial end faces and said annular member.

3. A device for electro-chemically measuring the concentration of oxygen in combustion gases, particularly those of internal combustion engines, comprising a housing having a passage which is formed with two spaced open ends with an inner circumferential shoulder intermediate said ends; a tubular member of ion-conducting solid electrolyte material having a closed-ended first portion which projects from one of said open ends, and a second portion which extends through said passage and is formed with an outer circumferential flange of which one axial end face faces towards said one open end and is supported by said shoulder and of which another axial end face faces away from said one open end, the interior of said tubular member being in communication with the ambient atmosphere and the exterior of said first portion being adapted for exposure to a flow of combustion gases, and the materials of said housing and of said tubular member having differential coefficients of thermal expansion and contraction; an electron-conductive inner electrode on an inner surface of said tubular member and being conductively connected with an outside terminal portion; an electron-conductive outer electrode on an outer surface of said tubular member and being conductively connected with said housing; compensating means comprising a discrete compensating member installed in said housing separate from but fixed with reference thereto and engaging said second portion of said tubular member, said compensating means being operative to compensate for said differential coefficients of said housing and of said tubular member so as to prevent development of cracks or loosening of the seal between said housing and said tubular member; and a body of pulverulent material accommodated in and filling a space defined by said tubular member, housing and compensating member, said body being at substantially constant pressure despite the occurrence of differential thermal expansion or contraction due to said differential coefficients.

4. A device for electro-chemically measuring the concentration of oxygen in combustion gases, particularly those of internal combustion engines, comprising a housing having a passage which is formed with two spaced open ends with an inner circumferential shoulder intermediate said ends; a tubular member of ion-conducting solid electrolyte material having a closed-ended first portion which projects from one of said open ends, and a second portion which extnds through said passage and is formed with an outer circumferential flange of which one axial end face faces towards said one open end and is supported by said shoulder and of which another axial end face faces away from said one open end, the interior of said tubular member being in communication with the ambient atmosphere and the exterior of said first portion being adapted for exposure to a flow of combustion gases, and the materials of said housing and of said tubular member having differential coefficients of thermal expansion and contraction; an electron-conductive inner electrode on an inner surface of said tubular member and being conductively connected with an outside terminal portion; an electron-conductive outer electrode on an outer surface of said tubular member and being conductively connected with said housing; compensating means comprising a discrete compensating member installed in said housing separate from but fixed with reference thereto and engaging said second portion of said tubular member, said compensating means being operative to compensate for said differential coefficients of said housing and of said tubular member so as to prevent development of cracks or loosening of the seal between said housing and said tubular member; a first ring of relatively soft material accommodated intermediate one of said axial end faces and said shoulder; and a second ring of relatively soft material accommodated intermediate the other of said axial end faces and said compensating member.

5. A device as defined in claim 4, said compensating member being an annular member, surrounding said second portion and being of a material having a coefficient of thermal expansion and contraction which compensates for said differential coefficients.

* * * * *